(12) United States Patent
Martin

(10) Patent No.: US 8,242,176 B2
(45) Date of Patent: Aug. 14, 2012

(54) BIOCIDAL ALDEHYDE COMPOSITION FOR OIL AND GAS EXTRACTION

(76) Inventor: Howard Martin, Rockville, MD (US)

( * ) Notice: Subject to any disclaimer, the term of this patent is extended or adjusted under 35 U.S.C. 154(b) by 328 days.

(21) Appl. No.: 12/584,650

(22) Filed: Sep. 9, 2009

(65) Prior Publication Data
US 2011/0060052 A1 Mar. 10, 2011

(51) Int. Cl.
A01N 33/12 (2006.01)
A61K 31/14 (2006.01)

(52) U.S. Cl. ........................................ 514/642; 514/643
(58) Field of Classification Search ........................ None
See application file for complete search history.

(56) References Cited

U.S. PATENT DOCUMENTS

| | | | | |
|---|---|---|---|---|
| 4,353,806 A | * | 10/1982 | Canter et al. | 507/229 |
| 5,128,051 A | * | 7/1992 | Theis et al. | 210/764 |
| 5,252,606 A | * | 10/1993 | Martin | 514/574 |
| 7,231,976 B2 | * | 6/2007 | Berry et al. | 166/291 |

FOREIGN PATENT DOCUMENTS
CN 1664048 A * 9/2005

OTHER PUBLICATIONS

"Pluronic PE types" Technical Information, Mar. 2005, published by the BASF Chemical Company.*

* cited by examiner

Primary Examiner — James H. Alstrum-Acevedo
Assistant Examiner — Daniel L Branson
(74) Attorney, Agent, or Firm — Ober, Kaler, Grimes & Shriver; Royal W. Craig

(57) ABSTRACT

A novel combination of a biocide (Glutaraldehyde or OPA), a surfactant, alcohol, and functional excipients for the oil and gas recovery industry. The surfactant is preferably a dual chain quaternary ammonium compound consisting of a mixture of alkyl dimethy-benzylammonium chlorides and alkyl dimethylethylbenzylammonium, that absorbs onto a surface and alters the free energy of that surface. The alcohol is preferably isopropyl alcohol. The functional excipients for the oil and gas recovery industry are a cellulose type proppant, a poloxamer wetting agent, a friction-reducing pluronic block copolymer, a drag reducing agent such as polethylene oxide, and a flocculating agent. The biocide may be OPA of the dialdehyde $C_6H_4(CHO)_2$ form, or Glutaraldehyde of formula $C_5H_8O_2$. Both will produce an inherent bacteriostatic effect and lower surface tension and thus aids in the spread of the dual quat on the biofilm covered surface where it is readily absorbed by the negative surfaces of proteins and bacteria. It thus serves as a binding agent between the dual quat and the application surface. This multi purpose component helps create the unique aspect of the formulation. The foregoing constituents are combined in preferred concentrations within acceptable ranges to provide a synergistic formulation that combines biocidal molecules in a biological chemical system that actively transports itself into the cells, through biofilm and cell wall/membranes, thereby overcoming penetration restraints to improve kill and kill time, without the need for activation or any time or temperature control. This is an effective example of synergistic complementarity.

9 Claims, No Drawings

BIOCIDAL ALDEHYDE COMPOSITION FOR OIL AND GAS EXTRACTION

BACKGROUND OF THE INVENTION

1. Field of the Invention

The present invention relates to chemical disinfection and sanitizing and, more particularly, to an improved biocidal aldehyde composition particularly suited for secondary oil and gas recovery.

2. Description of the Background

The purpose of disinfection is to reduce microbial contamination to an innocuous level. There is a widespread need for effective antimicrobials across diverse industries, including for oil and gas recovery (for treatment, penetration and removal of biofilm). Without a biocide, microorganism growth leads to biofilm formation, which contributes to corrosion, contamination of oil and gas, and degradation of drilling muds and fracturing. There are a few existing commercial biocides that purport to solve the need. For example, Dow® sells a line of AQUCAR™ water treatment microbiocides which include various proportions of glutaraldehyde alone or in combination with other biocides such as acetone or ammonium chloride. Glutaraldehyde is an important high level disinfectant/steriliant also used in other industries such as health care. It requires time and temperature control (residence time of 45-90 minutes for disinfection, and controlled temperature of from 20 C. to 25-30 C.). Glutaraldehyde requires activation and dating to make it useful. Thus, proper usage entails a three step procedure and meticulous record-keeping regarding date of activation.

A different aldehyde, orthophthaldehyde (OPA), has now come into use in the health care industry. Johnson and Johnson developed an original formulation in the late 1980s described in U.S. Pat. No. 4,851,449 and in subsequent continuation in part application(s). This OPA has been approved by the FDA as a high level disinfectant with a twelve minute disinfection time at 20-22 degrees C. Its sterilization time is listed between 24-32 hours. OPA interacts with amino acids and proteins of microorganisms. OPA is lipophilic, which improves its uptake in the cell walls. Thus, OPA has been shown to be another effective disinfectant/steriliant. The J&J OPA concentration is 0.55% by weight at a pH 3-9. It has been shown to be effective in a purely aqueous immersion solution. Metrex Research Corp. continues to sell a modified formulation referred to as OPA+, with an increased OPA concentration of 0.6% (0.05% more OPA), plus buffers, a corrosion inhibitor, and a chelating agent. In essence the formula is the same as the J&J product, with no faster kill time, but claims of 60% more treatment. However, if one looks at the mechanism by which OPA works it becomes biologically clear where the weaknesses lie. OPA is an aromatic dialdehyde. The severe test for cidal effectiveness are gram negative bacteria, mycobacteria and sporecoated organisms. OPA is not completely effective in clinical use at its concentration of 0.5% and pH 6.5. Failures occur and have been reported in literature surveys. The benzene ring of OPA is a planar, rigid structure. Therefore, OPA has no flexibility as a result of steric hinderance. In addition, OPA only reacts with primary amines. OPA is bactericidal at low concentrations to staphylococci and gram negative bacteria. The poor sporicidal activity is due to low concentration and low pH. It has been noted that if the temperature is raised from the normal 20 degrees C. to 30 degrees it improves. However, this is impractical. Regarding mycobacteria, a similar problem is present. The lipophilic aromatic component of OPA does not reliably penetrate the lipid-rich cell wall of mycobacteria and gram negative bacteria. Indeed, subsequent studies show that OPA exhibits selective bactericidal activity, good against *P. aeruginosa*, limited activity against mycobacterial strains. Shackelford et al., *Use of a New Alginate Film Test To Study The Bactericidal Efficacy Of The High-Level Disinfectant Ortho-Phthalaldehyde*, Journal of Antimicrobial Chemotherapy, 57(2):335-338 (2006). Despite the lingering issues, OPA has been suggested for use as a biocide in oil and gas recovery applications. See, U.S. Pat. No. 5,128,051 to Theis et al. issued Jul. 7, 1992 which discloses providing ortho-phthalaldehyde to aqueous systems susceptible to biofouling, including secondary oil recovery processes.

What is needed is a simple and improved one-step formulation using either glutaraldehyde or OPA for more effective disinfection/sterilization in industrial/commercial uses such as oil and gas recovery.

SUMMARY OF THE INVENTION

It is, therefore, an object of the present innovation to provide a novel strategy for potentiating and improving the cidal effectiveness of orthophthalaldehyde or glutaraldehyde by a synergistic formulation that combines cidal molecules with a biological chemical system that actively transports itself into the cells, through the biofilm and cell wall/membranes, thereby overcoming penetration restraints.

It is another object to improve cidal effectiveness against a broader range of refractory microorganisms within ecological and environmentally acceptable parameters, essentially yielding a green biocide.

In one embodiment designed for the oil and gas industry, these and other objects are accomplished by a novel combination of glutaraldehyde or OPA, a surfactant, alcohol, a proppant, friction reducing chemical additive, wetting agent, drag reducing agent, and flocculating agent. The surfactant is preferably a dual chain quaternary ammonium compound (a "dual quat") comprising a mixture of alkyl dimethyl-benzylammonium chlorides and alkyl dimethylethylbenzylammonium, that absorbs onto a surface and alters the free energy of that surface. The alcohol is preferably isopropyl alcohol. The OPA is the dialdehyde $C_6H_4(CHO)_2$, which produces an inherent bacteriostatic effect and lowers surface tension and thus aids in the spread of the dual quat on the biofilm covered surface where it is readily absorbed by the negative surfaces of proteins and bacteria. It thus serves as a binding agent between the dual quat and the application surface. Rather than OPA, a glutaraldehyde may be substituted in conjunction with the other constituents. The foregoing constituents are combined in preferred concentrations within acceptable ranges to provide a synergistic formulation that combines cidal molecules with a biological chemical system that actively transports itself into the cells, through the biofilm and cell wall/membranes, thereby overcoming penetration restraints to improve kill and kill time, without the need for activation or any time or temperature control.

Other objects, features, and advantages of the present invention will become more apparent from the following detailed description of the preferred embodiments and certain modifications thereof.

DETAILED DESCRIPTION OF THE PREFERRED EMBODIMENT

The present invention is a solution with a synergistic complementarity of constituents that combine to improve the cidal effectiveness of glutaraldehyde or orthophthalaldehyde through a biological chemical system to provide improved results. The present invention allows a one-step formulation for disinfection/sterilization for industrial/commercial uses and especially secondary oil and gas recovery, by addition to fracturing (frac) water as an aqueous solution additive. The unique chemo-biological formulation described herein improves the cidal effectiveness Glutaraldehyde or OPA by the addition of certain long chain polymer cationic surfactants, along with a proppant, friction reducing chemical additive, wetting agent, drag reducing agent, and flocculating agent, the foregoing combination creating a synergistic and unexpected improvement in biocidal effectiveness resulting in faster kill time.

The oil and gas recovery industry has a need for treatment, penetration and removal of biofilm. Biofilm harbors bacteria that attack surfaces such as steel, and that coalesces with oil in pipelines causing blockage. Biofilm occurs naturally by the bacteria, fungii, algae, protozoa developing it, as a protective mechanism. Surface microorganisms exist in planktonic suspension rather than in biofilm and are easier to kill. The biofilm exist in an exoploysaccharide matrix thereby having different characteristics than the planktonic types. This requires a biochemical approach rather than a purely chemical biocide as in the prior art. The dual chain quat also aids in the destruction and prevents proliferation of *desulfovibrio desulfurcans* (SRBs) of injected water in oil and gas recovery. When injected the quats will spread through the subterranean sand structures containing residual oil and displace the oil in the direction of the producing well. The Glutaraldehyde or OPA along with the dual chain quat work in synergy to kill the SRBs more effectively. Several groups have reported that biofilm bacteria exhibit more resistance to biocides. As in medicine, industrial surfaces (such as surfaces of storage tanks, pipelines, water circulating systems, and machinery) become colonized by biofilms. It is known that the anionic polysaccharide matrix (glycocalyx) affords considerable protection to these cells against antimicrobial agents. Essentially a physical barrier is erected against the penetration of the biocide. Along with the barrier concept other biological mechanisms are also involved such as enzyme formation, reduction of metabolism through quiescence, and general stress response leading to a new general biofilm phenotype. Thus, the oil and gas industry has a severe biofouling problem with the development of biofilm along with sulfate reducing bacteria that creates significant damage. The basic strategy of biofilm control is predicated on the use of chemicals to kill bacteria in the biofilm, to induce the natural sloughing of dead biofilm thus cleaning the surface. The chemical approach suffers from the limitation that the most effective antimicrobial agents do not penetrate the biofilm. It is very difficult to deliver enough cidal agent to destroy the bacteria within the biofilm, the sessile organisms. These insidious and coated bacteria must be destroyed in order for water pipelines to function and clean the oil. The biofilm contains amongst its variety of microorganisms, SRBs, algae, fungi, aerobic, anaerobic and facultative bacteria. Plank tonic type bacteria exist in an aqueous phase and are relatively easy to kill. It is however, the extracellular polymeric material that protects the attached or contained sessile organism that is the difficult one to eradicate. It is with these protected organisms that the present formulation excels, attacking and achieving the desired kill effect. It is noteworthy that in the industrial context the efficacy improves as the temperature rises. The illustrative tests were run at 20-22 C. but the one test run at 25-30 C. showed a significant reduction in time.

Currently, in the oil and gas recovery business, companies employ calibrated force to control the biofilm by overcoming the tensile strength of the matrix material without damaging the integrity of the surface. Hydraulic fracture or "fracking" is used to initiate oil and gas production in the shale recovery area. Fracking uses the hydrodynamic shear of water pump pressure to create fractures that extend from a borehole into rock formations. The fractures are maintained open by a proppant (a propping agent), usually a granular substance such as sand or mechanical such as aluminum pellets or ceramic, which prevent the fractures from closing. This is typically used in low permeability reservoirs and/or to re-stimulate production in old wells. To enhance recovery, the fracking technique is used with what is a slick water frac. This begs the need for a friction reducing chemical additive to allow water to be pumped faster and deeper into the formation. A secondary requirement is the need for a proppant that is biodegradable and will not clog or block the fluid. Therefore, a combination biocide, biodegradable proppant, and a soluble friction reducer would serve well. The above-described formulation may be modified slightly to provide an unconventional formula approach to this problem.

AIn accordance with the present invention, a core biocide either OPA of the dialdehyde $C_6H_4(CHO)_2$ form, or Glutaraldehyde of formula $C_5H_8O_2$, in alcohol-solution form, is modified by combining a Dual Chain Quat, Isopropyl Alcohol, and other functional excipients specifically for the oil and gas recovery industry. Specifically, the modification entails the addition of a proppant, friction reducing chemical additive, wetting agent, drag reducing agent, and flocculating agent to the above-described formulation, preferably replacing a small portion of the alcohol.

The proppant of choice is a cellulose type, preferably a water soluble binder such as methylcellulose, ethylcelluolose or hydroxymethylcellolose, which serve as an inactive filler, thickener and stabilizer. These materials are hydrophilic and highly absorbent thereby making an excellent proppant of a purely biologic non-toxic nature. Its biodegradability and natural occurrence makes this addition to the environment and ecosystem a green component. Being a straight chain polymer it becomes an extended stiff rod like formation. It forms via this conformation a micro fibril with high tensile strength because the hydroxyl group on the glucose molecule combines with oxygen molecules through a hydrogen bond thus giving shape, form and strength. Methylcellulose has value in zones of high heat as heat solidifies it giving it form and substance. It has inherent lubricity. Its derivatives can aid in water retention, surface slip resistance and maintain open time. A particular form, microcrystalline cellulose compacts well under high pressures and has a high binding capacity. It is hard, stable and yet can disintegrate rapidly. Cellulose is an ideal proppant excipient.

Furthermore, in order to facilitate the deep penetration by reduced frictional drag the addition of a wetting agent is required, and a poloxamer is preferred. This creates a high velocity hydro miscible vehicle. Poloxamers are nonionic triblock copolymers composed of a central hydrophobic chain of polyoxypropylene (poly(propylene oxide)) flanked by two hydrophilic chains of polyoxyethylene (poly(ethylene oxide)).

A monomeric polymer, preferably a pluronic block copolymer, is also added as a friction reducer for oil and gas recovery. The importance of this excipient and cellulose is recognized. Aqueous solutions of block copolymers are stable, soluble and exist as monomolecular micelles. They decrease surface tension as well as surface free energy. They reduce proppant flowback by strengthening the cellulose molecular structure. In oil and gas recovery the pluronic prevents the flowback via the proppant by its inherent adhesiveness. This also helps in agglomeration of the proppant.

The hydrodynamic flow may also be increased by improving flowability and penetration, thereby enhancing the shear forces. To achieve this, a drag reducing agent such as polethylene oxide may be used. What is required of the drag reducer is an agent that has a low coefficient of friction, low film thickness, and should be thixotropic or rheopectic. It needs to be effective at either low or high velocity for frac fluid usage. A fixed film thickness is necessary due to constant loading as well as low compressibility. What works is a water soluble resin such as a nonionic, high molecular weight water-soluble poly(ethylene oxide) polymer that brings lubricity, water retention, film formation and thickening into play. Dow® Polyox™ is an ideal brand of polyethylene oxide. This enables frac fluid to transport itself and penetrate deep into fractures. Polyox™ as a slip and drag reducer is compatible with the dual quats used by the above-described formula. They show little degradation at high pressure turbulence making them an ideal additive to the formulation. A reduction of splattering viscoelasticity is also necessary, and Polyox™ is an ideal flocculating agent for this purpose. It enables frac fluid to transport itself and penetrate deep into fractures.

In accordance with the present invention, a core glutaraldehyde or OPA is combined with the above-described Dual Chain Quat, Isopropyl Alcohol, and other functional excipients for the oil and gas recovery industry. Preferably, the core Glutaraldehyde or OPA, Dual Chain Quat, Isopropyl Alcohol and functional excipients are combined in the following preferred concentrations within acceptable ranges:

| Constituent | % by weight | Acceptable Range |
|---|---|---|
| OPA or Glutaraldehyde | 5% | 0.25-7% |
| Dual Chain Quat | .48% | .24-6% |
| Isopropyl Alcohol | 41% | 10-60% |
| methylcellulose, ethylcelluolose or hydroxymethylcellolose | 0.4% | 0.2-0.5% by weight |
| pluronic block copolymer | 0.7% | 0.01% to 3.00% by weight |
| poly(ethylene oxide) (Polyox ™) | 50 ppm or 0.5% | 10 ppm to 100 ppm (.1-1%) |

The balance of the solution is primarily water, plus inert additives as desired including Trienthanol Amine, Glycol Ether, and Sulfonic Acid. The pH range throughout can be pH 3 to pH 9.

The following examples illustrate the efficacy of the above-described embodiment in a formulation without the addition of a proppant, friction reducing chemical additive, wetting agent, drag reducing agent, or flocculating agent:

EXAMPLE 1

A formula of OPA—0.5%, Dual Quat—0.48%, and IPA—41% was applied to a challenge microorganism comprising *mycobacterium bovis* with an average cfu/carrier amount of $1.4\times10^5$—Acid fast stain confirmed *M. bovis*. Ten tubes were tested at 20 degrees C. for ten minutes and five minutes with an organic load of 5% in Kirchener medium. Test performed at 20° C. All passed at the 5 minute and 10 minute time and remained clear for 60 days.

EXAMPLE 2

The same formula concentration was used following AOAC guidelines against *Staph aureus, Ps. aeruginosa, S. choleraesuis, T. mentogrophytes*. 5% organic soil was added in synthetic broth. The carrier type used was stainless steel penicylinders. Test were performed at 20° degrees C. Ten carriers were exposed for 5 minutes. No carriers showed growth.

EXAMPLE 3

Sporicidal Sterility Test

Given formula concentration of OPA of 2%, dual chain quat 0.48%, and IPA of 42.0%, test was carried out using AOAC sporicidal guidelines. The challenge microorganisms were *Bacillus subtillus* and *Clostridium sporogenes*. Modified fluid thioglycollate medium was used. Temperature was 20 degrees C. Five carriers were tested of each organism. Exposure time was 10 hours. Incubation time was 21 days. Carriers were porcelain penicylinders and surgical threads. No growth was determined.

The above-described addition of a proppant, friction reducing chemical additive, wetting agent, drag reducing agent, and flocculating agent to the core formulation is well-suited for hydraulic fracture or "fracking" to initiate oil and gas production in the shale recovery area, combining biocidal molecules in a synergistic biological chemical system that actively transports itself into the cells, through biofilm and cell wall/membranes, thereby overcoming penetration restraints to improve kill and kill time, without the need for activation or any time or temperature control. This is an effective example of synergistic complementarity.

Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A biocidal formulation comprising an aldehyde selected from the group consisting of glutaraldehyde and orthophthataldehyde within a range of concentration from 0.25% to 7% by weight of said biocidal formulation, a dual chain quaternaly ammonium compound, isopropyl alcohol, proppant comprising a microcrystalline cellulosic compound selected from the group consisting of methylcellulose, ethylcellulose and hydroxymethylcellulose, a block copolymer defined by monomolecular micelles, a flocculating agent consisting of a nonionic triblock poloxamer copolymer, and water, combined to yield a pH within a range of from 3 to 9.

2. A biocidal formulation containing an aldehyde selected from the group consisting of orthophthalaldehyde and giutaraldchyde within a range of concentration from 0.25% to 7% by weight of said biocidal formulation, a dual chain quaternary ammonium compound, microcrystalline cellulosic proppant, a friction-reducer consisting of aqueous monomer block copolymer defined by monomolecular micelles, a wetting agent consisting of triblock non-ionic copolymer surfactant, and water, combined to yield a pH within a range of from 3 to 9.

3. The biocidal formulation according to claim 1 wherein said dual chain quaternary ammonium compound consists of equal values of N-alkyl dimethylbenzyl ammonium chloride- and N-alkyl dimethylethylbenzyl ammonium chloride.

4. The biocidal formulation according to claim 1 wherein said isopropyl alcohol comprises a range of from 10.00%-60.00% by weight.

5. The biocidal formulation according to claim 1 further comprising excipient cellulose of from 0.20% to 0.5% by weight.

6. The biocidal formulation according to claim 1 further comprising the excipient block copolymer, in from 0.01% to 3.00% by weight.

7. The biocidal formulation according to claim 1 further comprising non-ionic excipient copolymer surfactant, polyethylene oxide, in approximately 10 ppm to 100 ppm.

8. The biocidal formulation according to claim 1 in aqueous form.

9. The biocidal formulation according to claim 1 to reduce biofouling and improve frac fluids in the oil and gas industry.

* * * * *